United States Patent [19]

Soli et al.

[11] Patent Number: 4,813,417
[45] Date of Patent: Mar. 21, 1989

[54] SIGNAL PROCESSOR FOR AND AN AUDITORY PROSTHESIS UTILIZING CHANNEL DOMINANCE

[75] Inventors: Sigfrid D. Soli, Pine Springs; Christopher van den Honert, Maplewood, both of Minn.

[73] Assignee: Minnesota Mining and Manufacturing Company, St. Paul, Minn.

[21] Appl. No.: 25,524

[22] Filed: Mar. 13, 1987

[51] Int. Cl.$^4$ .................. A61N 1/00; H05G 00/00
[52] U.S. Cl. .................................. 128/420.5
[58] Field of Search ............ 128/420.6, 419 R, 420.5, 128/710, 731, 715

[56] References Cited

U.S. PATENT DOCUMENTS

| | | | |
|---|---|---|---|
| 4,289,935 | 9/1981 | Zollner et al. | 128/420.6 |
| 4,400,590 | 8/1983 | Michelson | 128/420.6 |
| 4,403,118 | 9/1983 | Zollner et al. | 128/420.5 |
| 4,515,158 | 5/1985 | Patrick et al. | 128/420.6 |
| 4,528,689 | 7/1985 | Katz | 128/715 |
| 4,532,930 | 8/1985 | Crosby et al. | 128/420.6 |

OTHER PUBLICATIONS

Sachs and Young, "Encoding of Steady-State Vowels in the Auditory Nerve: Representation in Terms of Discharge Rate", 66 *Journal of the Acoustical Society of America*.

Walker and Dent, "Functional Description of a Prototype Portable Four Channel Analog Processor for an Auditory Prosthesis", Appendix B and Setting the Four-Channel Analog Processor for an Arbitrary Sine-Wave Input, Appendix C (1986).

Young and Sachs, "Representation of Steady-State Vowels in the Temporal Aspects of the Discharge Patterns of Populations of Auditory-Nerve Fibers", 66 *Journal of the Acoustical Society of America*, pp. 1381-1403 (1979).

Primary Examiner—Francis Jaworski
Assistant Examiner—George Manuel
Attorney, Agent, or Firm—Donald M. Sell; William D. Bauer

[57] ABSTRACT

A multichannel signal processor for and an auditory prostheses utilizing such a signal processor having a plurality of filters each passing a different center frequency providing a set of filtered signals representative of the auditory content of the electrical input signal relative to its respective center frequency. A plurality of gating mechanisms individually coupled to the filter signals pass an output signal at a level above the perceptual level of the person when the filtered signal is above a predetermined level. The predetermined level is individually determined such that the output is past above the perceptual level only when the level of the filtered signal to which the gating means is coupled is likely to be among the larges of the filtered signals of all of the plurality of filters. Thus the multichannel signal processor in auditory prosthesis can have a combined stimulated signal which contains some, but not all, channels, namely those channels whose amplitude of signal is likely to rank among the highest compared to the amplitude of the remaining channels. In a preferred embodiment, such a channel dominant signal processor will help preserve periodicities created by sharply tuned band pass filters.

12 Claims, 7 Drawing Sheets

SIGNAL PROCESSOR FOR AND AN AUDITORY PROSTHESIS UTILIZING CHANNEL DOMINANCE

BACKGROUND OF THE INVENTION

The present invention relates generally to auditory prostheses and signal generators for auditory prostheses. More particularly, the present invention relates to such signal processors employing a plurality of band pass filters.

Various types of multichannel auditory prosthetic devices exist in the art.

One example of a multichannel auditory prosthesis is described in U.S. Pat. No. 4,400,590, Michelson. Michelson discloses a system that uses the theory that differing places along the cochlea respond as differing frequencies to the brain. Thus, band pass filters break up the incoming auditory signal into a plurality of frequency bands. These signals are than applied directly to electrode locations along the cochlea. In theory those locations which correspond its associated frequency band.

Another example of a multichannel auditory prosthetic device, is described in U.S. Pat. Nos. 4,289,935, Zollner et al and 4,403,118, Zollner et al. The system debcribed in the Zollner et al patents uses a set of band pass filters to generate frequency bands to turn on and off, or to modulate, oscillators (tone generators) whose outputs are then summed and transmitted to a hearing aid.

Both of the Michelson and Zollner et al multichannel auditory prosthetic devices, however, have been less than completely successful in obtaining open set speech comprehension without the use of visual aids;

Young and Sachs, in a 1979 article, "Representation of Steady-State Vowels in the Temporal Aspects of the Discharge Patterns of Auditory Nerve Fibers", 66 *Journal of the Acoustic Society of America*, pp 1381–1403, noted that spectral information is represented in the timing patterns of auditory nerve discharges. They determined the energy at a given frequency by examining temporal responses only among neurons whose center frequencies were close to that frequency.

SUMMARY OF THE INVENTION

The present invention provides a signal processor for an electrical input signal intended to represent sound to a person and adapted to be utilized in conjunction with an auditory prosthesis. A plurality of filters, each passing a different center frequency, each provide a filtered signal representative of the auditory content of the electrical input signal relative to its respective center frequency. A plurality of gating mechanisms, preferably operating as nonlinearities, are individually coupled to the filtered signals. Each of the gating mechanisms passes an output signal at a level above the perceptual level of the person when the filtered signal is above a predetermined level. The predetermined level is individually determined such that the output is passed above the perceptual level only when the level of the filtered signal to which the gating mechanism is coupled is likely to be among the largest of the filtered signals from all of the plurality filters.

In multichannel signal processing devices, an electrical input signal may provide outputs from a plurality of individual filters which are quite complex in nature. This is particularly true where the plurality of filters are sharply tuned filters, or resonators creating output signals which contain periodicities representative of the energy content of the input signal although the present invention is applicable to other filter sets as well. In such situations, the periodicities combined either in a summer or combined in the cochlea when multiply stimulated may produce undesirable channel interactions. A single processor having a gating mechanism constructed as described above can reduce undesirable interactions between periodicities from individual filters, channels interactions, which can degrade the spectral to temperal properties of the resonating filters and can reduce the likelihood of the production of unpredictably loud sensations to the patient.

For example, if a nine or ten channel signal processor, or auditory prosthesis, is provided it may be desirable to convey information to the patient from only a subset of those channels at any one given instant of time. For example, it may desirable that only five of the nine or ten channels will be active in conveying information above the patient's perceptual level at one given instant of time. Threshold levels are set in the nonlinearities such that only channels whose probable rank in dominance among the other channels is among the largest in amplitude as compared to the electrical outputs of the other corresponding channels.

Previous methods for reducing the number of simultaneously active channels involve ongoing comparisons of the amplitudes in each channel followed by the selection of the highest amplitude channels. The real-time computations required to compare and rank all channels and then select the dominant channels are time consuming and are not reasonably feasible for many real-time multichannel processing applications especially if a large number of channels are used. The present invention provides an alternative, statistically based approach to the selection of dominant channels that is feasible for real-time multichannel processing applications. Representative channel rank and amplitude statistics can be developed from laboratory analysis of speech processed through a computer simulation of a multichannel processor. From these statistics, threshold parameters for each channel can be identified such that each channel exceeds its threshold value only when it is likely to be one of the highest ranking (i.e. dominant) channels. Dominant channels are defined probablistically rather than exactly by this mechanism. However, the relationship between a channel's dominance and its perceptual importance in speech is also probablistic. Channel threshold parameters can be implemented in a look up table in a real-time processor obviating the need for ongoing real-time comparision computations between channels to select dominant channels.

BRIEF DESCRIPTION OF THE DRAWINGS

The foregoing advantages operation and construction of the present invention will become more readily apparent from the following figures in which.

DETAILED DESCRIPTION OF THE PREFERRED EMBODIMENTS

Figure 1:
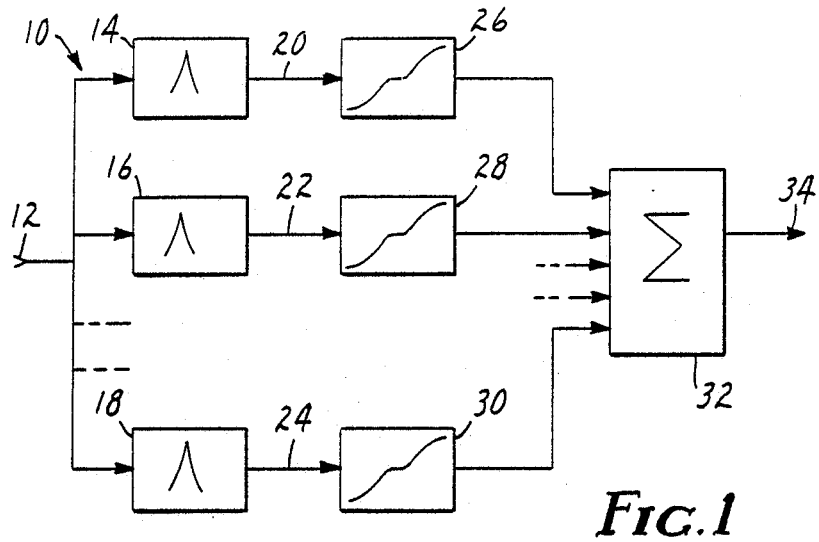
FIG. 1 is a simplified block diagram of the signal processor of the present invention.

Work by Young and Sachs has demonstrated that spectral information is well represented in the timing patterns of auditory nerve discharges. In their analysis, they determined the energy at a given frequency by examining temporal responses only among neurons whose center frequencies were close to that frequency.

The auditory central nervous system may perform a similar analysis, ignoring inappropriate periodicities, in responding only to appropriate ones, i.e., those close to the inverse of the center frequency for each individual nerve fiber. This ability to ignore an inappropriate periodicity on a nerve fiber can effectively explain the very good speech recognition achievable with single electrode cochlear implants. Periodic events corresponding to both the fundamental and the formant frequencies may exist in a single electrode stimulus waveform. With appropriate equalization, each of these periodicities will appear in the temporal discharge patterns of neurons across the entire cochlea. However, they will be ignored by the central nervous system except when they occur at the corresponding appropriate sites along the cochlea. For example, a complex stimulus signal containing both 500 Hertz and 200 Hertz components includes some events in the time domain which occur at 2 millisecond intervals and some which occur at 5 millisecond intervals. Such a stimulus signal delivered electrically to the cochlea would elicit neuronal impulses at both 2 millisecond and 5 millisecond intervals. These impulses would be elicted everywhere along the cochlea but the two millisecond intervals would be ignored except from the 500 Hertz neurons. Similarly, the 5 millisecond intervals would be ignored except from the 200 Hertz neurons. This illustrates that a single stimulating electrode, stimulating many neurons, can nevertheless deliver information about more than one frequency.

However, it is recognized that the number of different periodicities which may be contained on a single electrode may be limited. For example, if a single electrode attempts to convey a large number of differing periodicities, the combination may create additional periodicities not present in the original signal which could confuse the auditory central nervous system. For example, if 50 different periodicites were occuring on a particular neuron, the appropriate ones, e.g., 0.5 millisecond for a two kiloHertz fiber, might occur too rarely to be detected by the nerve fiber. This limitation can be overcome by the use of multiple electrodes each of which stimulates a spatially distinct group of neurons. It would then be unnecessary for one electrode, or electrode pair, to deliver all of the periodicities contained in the incoming signal. Rather, each electrode or electrode pair, would deliver only intervals corresponding to the center frequencies of the fibers within its locus or spatial range of excitation. This system has the potential to increase dramatically the frequency resolution afforded by multiple electrode auditory prosthetic devices which depend on spatial selectivity for achieving frequency differentiation.

A simplified block diagram of a signal processor to achieve the appropriate periodicities discussed above is illustrated in FIG. 1. The signal processor 10 receives an electrical input signal 12. The electrical input signal 12 is supplied to a plurality of sharply tuned band pass filters 14, 16 and 18. These band pass filters 14, 16 and 18 are less than critically damped and provide an electrical output signal 20, 22 and 24. These band pass filters have an impulse response which is oscillatory. In a preferred implementation, each of the band pass filters 14, 16, and 18 has a Q(3 dB) of more than 0.5. The sharply tuned band pass filters 14, 16 and 18 operate as resonators so that the output signals 20, 22 and 24, respectively, contain periodicities corresponding to the energy in the electrical input signal 12 corresponding to the center frequency to which band pass filters 14, 16 and 18 are tuned. Output signals 20, 22 and 24 are routed through nonlinearities 26, 28 and 30, respectively. Nonlinearities 26, 28 and 30 may operate to compress output signals 20, 22 and 24 so that the dynamic range of the signal present may be fitted into the dynamic range remaining in the person to be stimulated. Nonlinearities 26, 28 and 30 also perform an important gating or threshold, function to be described later. In one embodiment, the outputs of nonlinearities 26, 28 and 30 are then summed in summer 32 and a single output signal 34 is provided which contains the periodicites present in electrical input signal 12. Output signal 34 may then be provided to the remainder of an auditory prosthesis to be delivered to an electrode to electrically stimulate the person or may be povided to an electrical to auditory transducer in order to acoustically stimulate a person. While the block diagram of the signal processor in FIG. 1 illustrates three separate band pass filters, resonators, 14, 16 and 18 it is to be recognized and understood that more resonators or fewer resonators may be desirable in a particular signal processor and that three are illustrated for illustrative purposes only.

Since too many periodicites present in output signal 34 may confuse the individual neurons of the auditory central nervous system, only those output signals 20, 22 and 24 which are largest in amplitude should be applied to the auditory central nervous system and, hence, be contained in output signal 34. In a preferred embodiment of the signal processor of FIG. 1, each band pass filter, resonator, 14, 16 and 18 is a very narrow filter whose purpose is to generate an output signal 20, 22 and 24 which is periodic if the electrical input signal 12 has significant energy near its center frequency. The period of that signal is the inverse of the frequency being passed through the resonator 14, 16 and 18. The nonlinearity 26 has a "compressive region" which serves to compress the resonator output into a dynamic range appropriate for the cochlear implant and, importantly, a "deadband" to mask out low level signals. Signals appear at the outputs of only those nonlinearities 26, 28 and 30 whose input signals 20, 22 and 24 exceed the deadband threshold. The nonlinearities 26, 28 and 30 do not alter the periodicities contained in those signals. The nonlinearities 26, 28 and 30 determine whether they are large enough to be passed on and to limit them from becoming too large, i.e. compression. As the signals from nonlinearities 26, 28 and 30 are summed in summer 32, a composite output signal 34 is provided. Note that only some of the signals 20, 22 and 24 are usually actually present in output signal 34 because only those signals 20, 22 and 24 which have sufficient amplitude to exceed the deadband of nonlinearities 26, 28 and 30 actually appear at summer 32. Thus, output signal 34 may have more than one periodicity but not so many periodicities that the periodicities are lost.

Figure 2:
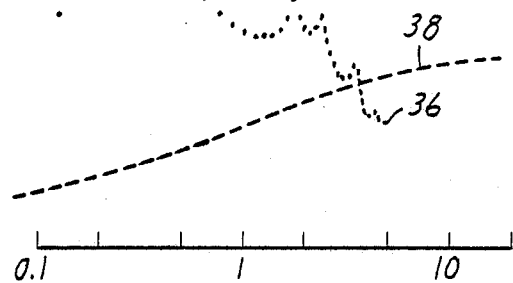
FIG. 2 is a representation of the frequency spectrum of the vowel "eh"
Figure 3:
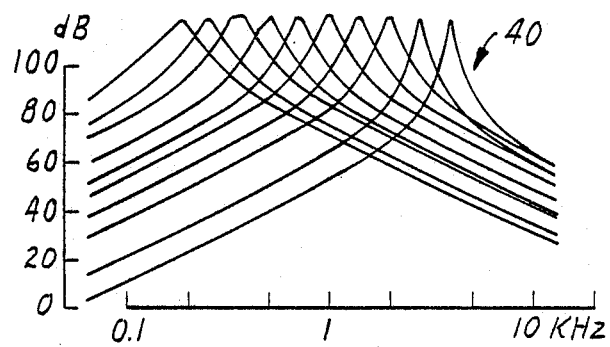
FIG. 3 illustrates a transfer function of the band pass filters.
Figure 4:
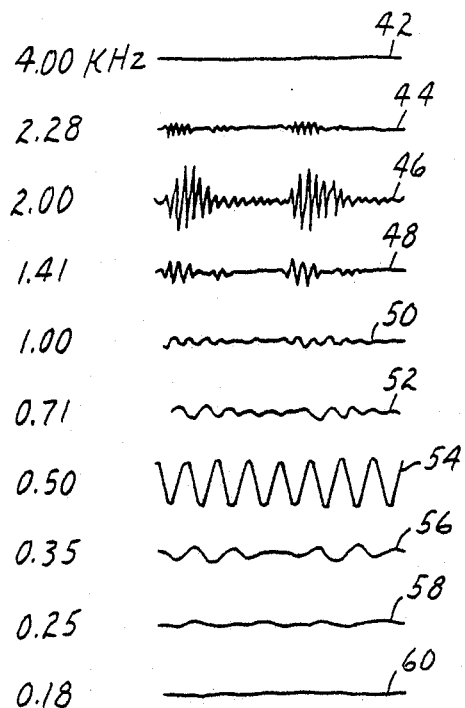
FIG. 4 illustrates the time domain band pass filter outputs with a stimulus as defined in FIG. 2.

FIG. 2 shows the frequency spectrum of a vowel "eh" 36, before appropriate high frequency emphasis 38 at 30 dB per octave. The spectrum of the vowel "eh" 36 shows formant peaks near 0.5 kiloHertz and 2.0 kiloHertz. The frequency spectrum of the vowel illustrated in FIG. 2 is then applied to each of ten resonators 40 illustrated in FIG. 3 tuned at one-half octave intervals between 0.177 kiloHertz and 4.0 kiloHertz. The transfer function of resonators 40 correspond to resonators 14, 16 and 18 of a signal processor as illustrated in FIG. 1. The time domain output signals of these resonators 40 are illustrated in FIG. 4 by reference numerals 42–60. Notice that the time domain output signals 54 and 46 are the greatest in amplitude which corresponds to the 0.5 kiloHertz and 2.0 kiloHertz formant peaks of the frequency spectrum of FIG. 2. Thus, resonators 40 have created periodicites, mainly signals 54 and 46, which corresponds to the frequency of energy contained in the input signal of the vowel 36.

Figure 5:
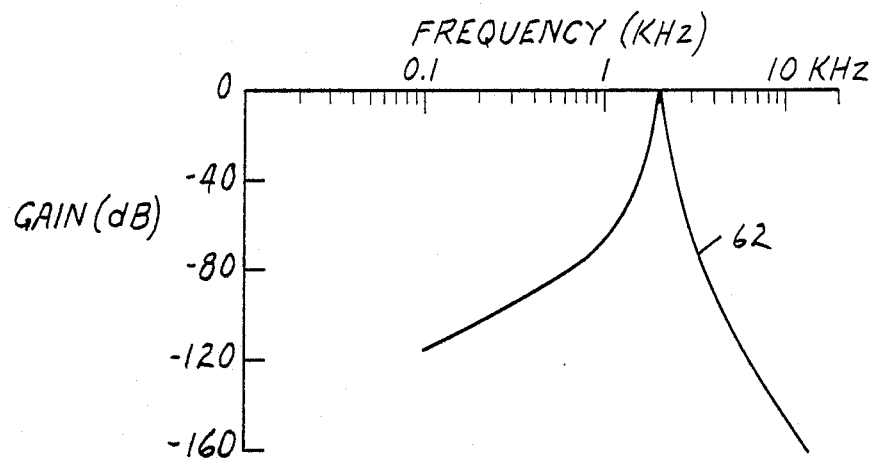
FIG. 5 illustrates the amplitude characteristics of a preferred band pass filter.
Figure 6:
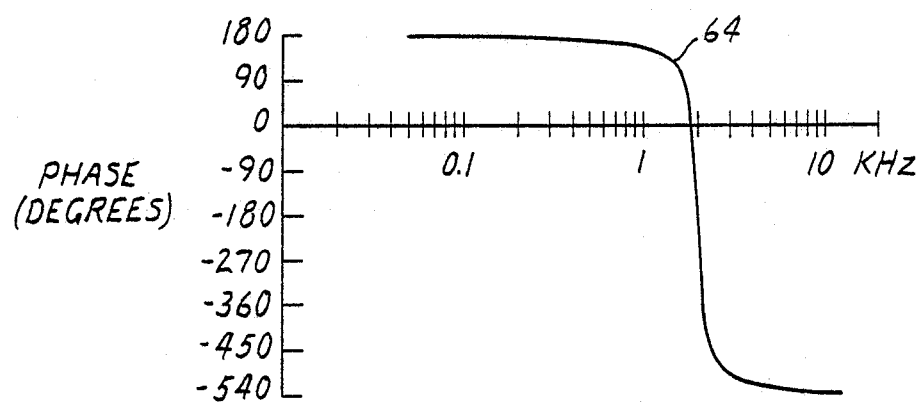
FIG. 6 illustrates the phase characteristic of a preferred band pass filter.

The amplitude characteristic 62 of a preferred bandpass filter is illustrated in FIG. 5. Correspondingly, the phase characteristic 64 of a preferred band pass filter is illustrated in FIG. 6. The sharpness of each, band pass filter is measured by the Q of the band pass filter. The Q is determined by dividing the center frequency of the filter by the bandwidth of the filter as measured by the frequencies which are given amount dB down from the peak of the filter response. Thus, the value of Q must be expressed in terms of Q for a particular dB. If the bandwidth of the filter response as measured 3 dB down from the peak is a given frequency width and that frequency width is divided into the center frequency, the Q(3 dB) is obtained. Similarly, a Q(10 dB) can be obtained by taking the bandwidth at the 10 dB down points on the amplitude curve 62 of FIG. 5. Thus, it can be seen that the higher the value of Q the more sharply tuned the individual filter. Also, it can be seen that a given filter will have a Q(3 dB) which is of a greater numerical value than its corresponding Q(10 dB). For purposes of the present invention, it is preferred that the filter response be underdamped, i.e., the Q(3 dB) be more than 0.5. The filter response is preferred to have an oscillatory response to a step or impulse input. This is referred to its impulse function being oscillatory. As illustrated in FIG. 6, the phase characteristic of the filter is preferred to be positive for frequencies below the center frequency of the filter, have a sharp transition through zero at the center frequency and be negative for frequencies greater than the center frequency of the filter. This mimics the phase characteristic of the individual neurons of the auditory central nervous system.

Figure 7:
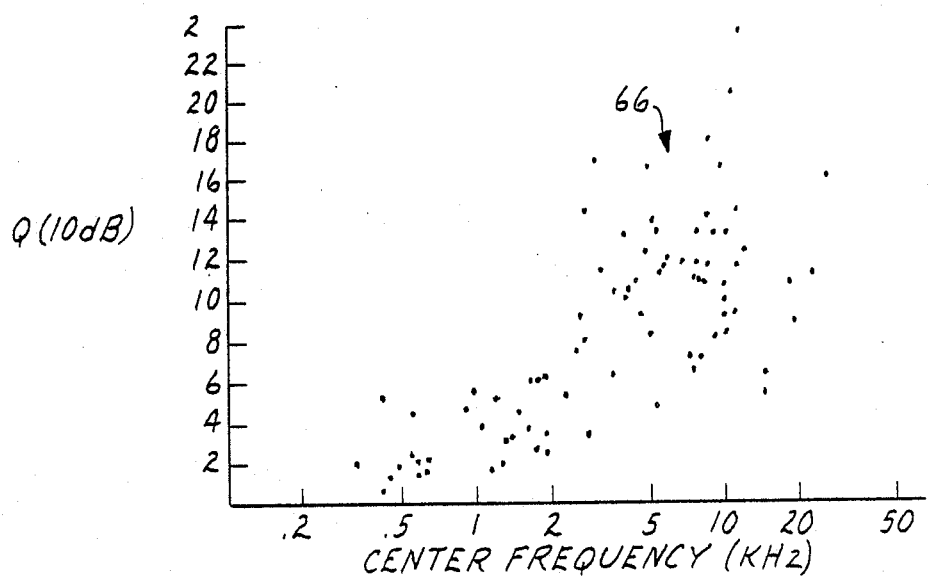
FIG. 7 illustrates the actual Q's of neurons for various frequencies plotted as a function of center frequency.

In a preferred embodiment, the Q of each individual filter should match the Q actually measured for nerve fibers with similar center frequencies. Such Q's have been measured by Kiang et al "Discharge Patterns of Single Fibers in the Cat's Auditory Nerve", MIT Research Monograph 35, Library of Congress 6614345 (1965). The Q's 66, as determined by Kiang et al are depicted graphically in FIG. 7. Here the Q's 66 illustrated are Q(10 dB) values.

Figure 8:
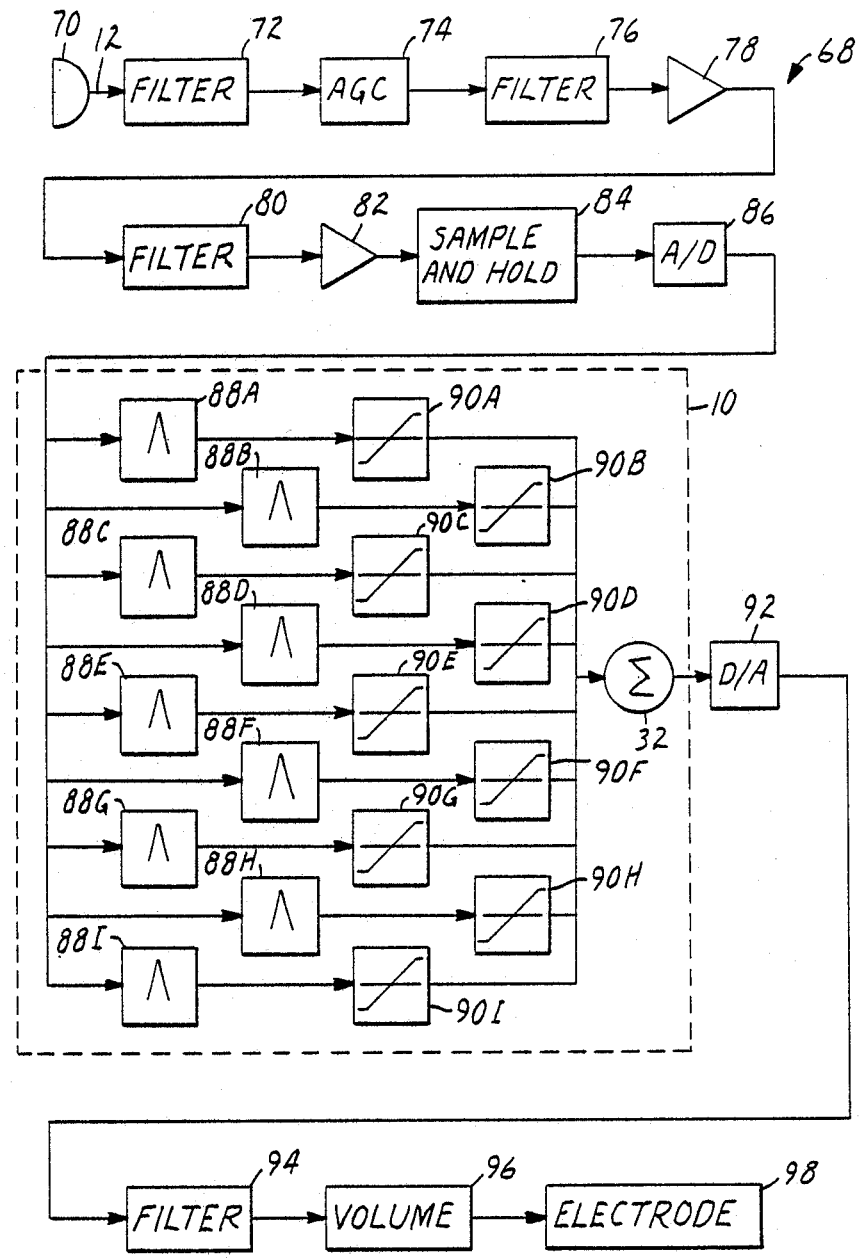
FIG. 8 is block diagram of a preferred embodiment of the auditory prosthesis of the present invention.

FIG. 8 represents a block diagram of a preferred embodiment of a auditory prosthesis 68 of the present invention. A microphone 70 transforms a given auditory signal into an electrical input signal 12. The electrical input signal 12 is fed to a switchable lowcut filter 72 to optionally provide noise supression for low frequency noise components. An automatic gain control 74, which may have an external sensitivity control, limits the dynamic range of the electrical input signal 12. A pre-emphasis filter 76 boosts the high frequency components common in speech signals. A gain element, amplifier, 78 compensates for internal signal losses. An anti-aliasing filter 80 prevents corruption of the signal by frequencies above the Nyquist frequency of 5 kiloHertz. Another gain element, amplifier, 82 again compensates for internal losses. A sample and hold circuit 84 and analog to digital converter element 86 convert the signal to a digital representation. Elements 70, 72, 74, 76, 78, 80, 82, 84 and 86 are conventional and well known in the art. Elements 72, 74, 76, 78, 80, 82 and 84 are optional and are illustrated here as being part of the preferred embodiment of the auditory prosthesis 68. A digital signal processor 10 corresponds to the signal processor 10 illustrated in FIG. 1. Signal processor 10 contains a plurality, namely nine, band pass filters 88A–88I, each passing a different center frequency. In a preferred embodiment, filter 88A has a center frequency of 0.5 kiloHertz; filter 88B, 0.5 kiloHertz; filter 88C, 0.71 kiloHertz; filter 88D, 0.91 kiloHertz; filter 88E, 1.17 kiloHertz; filter 88F, 1.5 kiloHertz; filter 88G, 1.94 kiloHertz; filter 88H, 2.5 kiloHertz and filter 88I, 3.2 kiloHertz. The individual outputs of filters 88A–88I are passed to nonlinearities 90A–90I. The outputs of these nine nonlinearities 90A–90I are then provided to summer 32 where the signals are digitally summed together and converted back into an analog signal by digital to analog converter 92. In inverse filter 94 is provided to compensate for any subsequent known output transmission characteristics of the auditory prosthesis. An internal volume control 96 is supplied to allow for appropriate amplitude adjustment by the person and the signal is then provided to an electrode, or electrode pair, 98. Elements 92, 94, 96 and 98 are conventional and well known. Elements 94 and 96 are optional. In a preferred embodiment, microphone 70 is a Knowles EA1934 with 3 dB downpoints at 250 Hertz and 8 kiloHertz. In a preferred embodiment, lowcut filter 72 is a 6 dB per octave lowcut filter with corner frequencies switch selectable by the patient at either 250 Hertz or 500 Hertz. In a preferred embodiment, automatic gain control circuit 74, has an attack time of approximately 1 millisecond and a release time of approximately 2 seconds. The threshold is determined by a sensitivity control. In a preferred embodiment, preemphasis filter 76 is a 6 dB per octave high pass filter with a corner frequency at 4 kiloHertz. Pre-emphasis filter 76 is intended to compensate partially for the 10–12 dB per octave high frequency roll off in the long term spectrum of speech, thus, decreasing the loss of amplitude resolution in high frequency components of speech. Gain element 78, anti-aliasing filter 80, gain element 82, sample and hold element 84, analog to digital converter element 86, digital to analog converter element 92, inverse filter 94, volume control 96 and electrode 98 are conventional elements well known in the art. In the preferred embodiment of the auditory prosthesis 68, filters 88A-88I are digitally implemented at their indicated center frequencies. In a preferred embodiment, filter 88A and filter 88B have a Q(10 dB) equal to 3, filters 88C, 88D and 88E have a Q(10 dB) equal to 4, filter 88F has a Q(10 dB) equal to 5, filter 88G has a Q(10 dB) equal to 6, filter 88H has a Q(10 dB) equal to 7 and filter 88I has a Q(10 dB) equal to 8. The digital implementation of all filters are preferred to be fourth order. The digital implementation of such filters are conventional in design and are well known although not used for this purpose or function.

Figure 9:
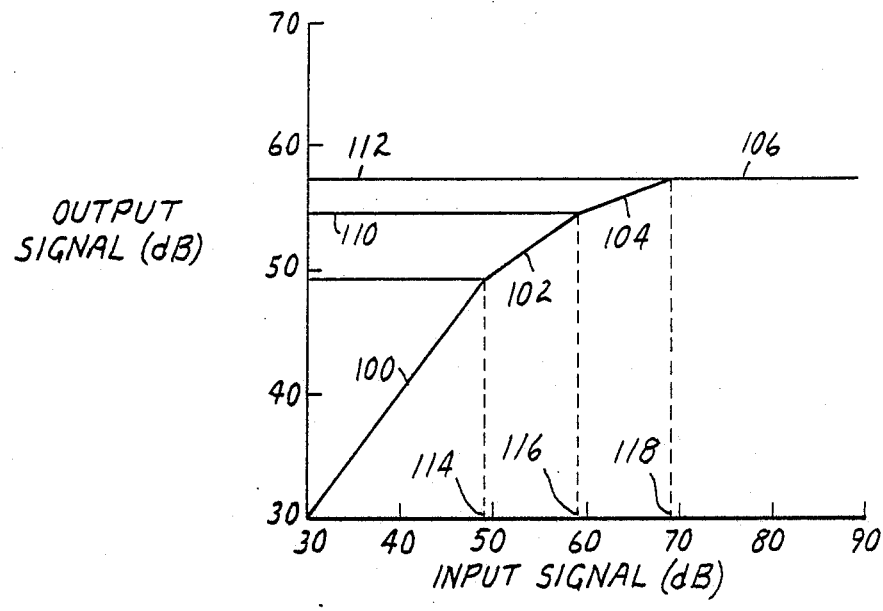
FIG. 9 is an exemplary input/output function of a nonlinearity.

The implementation of nonlinearities 90A-90I is a function of input fitting and output fitting. Each nonlinearity maps a range of instantaneous input signal levels as produced by resonators 88A-88I, respectively into a range of instantaneous output signal levels. The mapping function has a linear region 100, a cascade of two power functions 102 and 104 and a saturation function 106 as shown in FIG. 9. By mapping the input levels into the saturation region 106 or into either of the power function regions 102 and 104, any range of input levels can be compressed into the desired output range. The output range is tailored to the subject's electrical dynamic range. The input range is also set as part of the input fitting to map a desired range of filter output levels into the compressive region of the output range and thus into the subject's electrical dynamic range.

The output range is fitted to the subject with three nonlinearity parameters Y(min) 108, Y(mid) 110 and Y(max) 112. Y(min) 108 defines the boundary between the linear function 100 and the first power function 102. Y(min) 108 is set at the subject's perceptual threshold, i.e., the level below which the subject has no auditory perception Y(max) 112 defines the boundary between the second power function 104 and the saturation function 106. Thus, output levels greater than Y(max) 112 are not produced Y(max) 112 for an individual subject is determined in conjunction with the uncomfortable loudness level of the individual subject. Y(mid) 110 which corresponds to the boundary between the first power function 102 and the second power functions 104 is defined as the value of Y(min) 108 plus 0.66 times the quantity Y(max) 112 minus Y(min) 108.

The input dynamic range of each nonlinearity 90A-90I is fitted to the distribution of the instantaneous signal levels in speech measured at the output of the individual filters 88A-88I. Three parameters X(min) 114, X(mid) 116 and X(max) 118 which define corresponding coordinate pairs with the Y values 108, 110 and 112 are used to fit the nonlinearity. Two optional approaches in fitting the X values 114, 116 and 118 can be utilized.

In a first nonpreferred approach, the 95th percentile of the distribution of the instantaneous output levels from each filter 88 is computed for a large sample of processed speech. X(max) 118 is set to this value. Using this value, 5% of the filter output for an individual channel is mapped into the saturation function 106 X(min) 114 is then set to a value 20 dB below X(max) 118 and X(mid) 116 is set halfway between X(max) 118 and X(min) 114. These parameters map approximately 40%-50% of the input speech levels into the subject dynamic range for each channel. With the remaining 50%-60% falling at or below threshold in the linear function 100, this approach mixes a large number of channels which contain suprathreshold components. Thus, the composite signal from summer 32 may exhibit a large number of periodicities.

In a present invention, a "channel dominance" approach is utilized in which only the outputs from filters 88A-88I whose signals are likely to be the largest pass or are gated through nonlinearities 90A-90I and, thus, are gated onto summer 32 and, hence, whose periodicities are present in the output signal which are above the patient's perceived threshold level. In this way, the number of periodicities present in the summed signal are reduced and appropriate possible periodicity interactions are also reduced. This is accomplished by increasing the values of the X parameters 114, 116 and 118 so that a greater percentage of the speech input signals would be mapped into the linear function 100 and, thus, be below the perceptual level of the patient. Utilized in this manner, only the highest amplitude or dominant channels are at suprathreshold levels.

Figure 11:
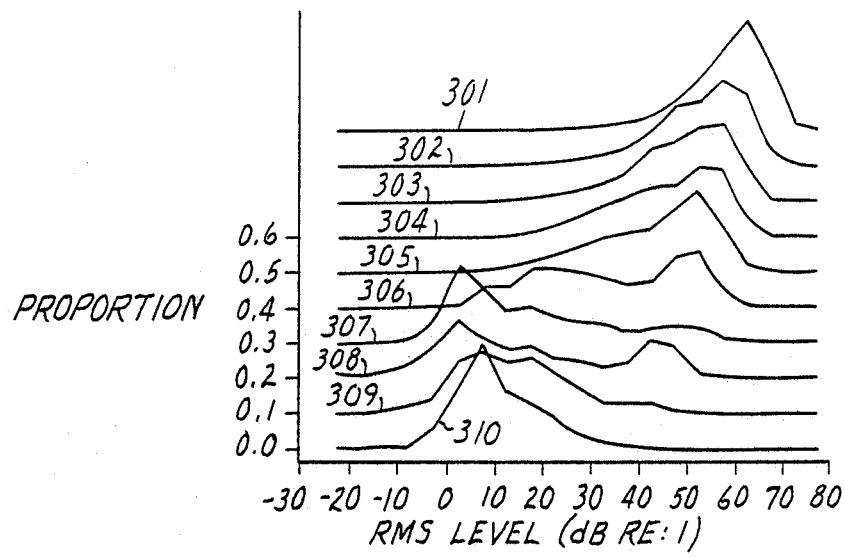
FIG. 11 is a plot of relative dominance of one channel as a function of frequency.
Figure 12:
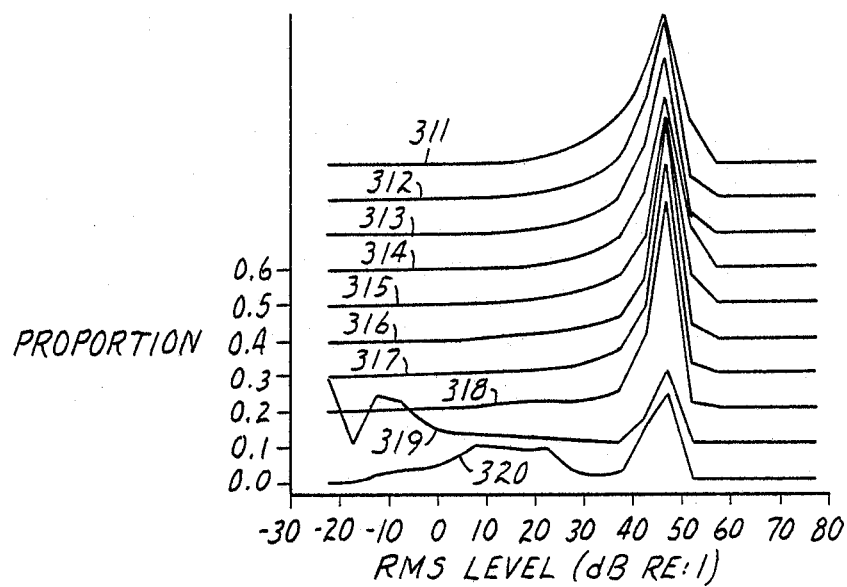
FIG. 12 is a plot of relative dominance of another channel as a function of frequency.

FIGS. 11 and 12 represent amplitude distributions for two exemplary channels in an exemplary signal processor. A large sample of recorded speech materials were processed by computer simulation and the computations compared and ranked all channels contained in the auditory prosthesis previously illustrated in FIG. 8. FIG. 11 represents channel 4 of the signal processor 10 of FIG. 8 having a center frequency of 500 Hertz. The horizontal axis represents the RMS level of this channel expressed in decibals relative to a base of 1. The vertical axis represents the proportion of the time instances that this channel has the indicated rank. Line 301 in FIG. 11 represents the amplitudes of the 500 Hertz channel only for those instances when it is the highest ranked channel in terms of amplitude among all of the channels of the signal processor. Similarly, curve 302 represents those amplitudes only for those instances when this channel is ranked second in amplitude. A corresponding relationship holds true through curve 310 in which displays the amplitudes only for those instances when the 500 Hertz channel was the lowest ranking channel. From the distributions exhibited in FIG. 11, it can be seen that the 500 Hertz channel exhibits a contingent relationship between rank and amplitude with contingent channels like this 500 Hertz channel illustrated in FIG. 11 a channel threshold can be defined such that the channel will be activated only when it is likely to be one of the highest ranking or dominant channels. For example, a channel threshold set at 50 decibals would include most of the instances when the channel was one of the top five channels and would exclude most of the instances when the channel was one of the bottom five channels.

In the present example then X(min) 114 is set at 50 decibals X(max) 118 is set at a level to include almost all of the remaining available signals, in this example 70 decibals X(mid) 116 is set at the midpoint between X(min) 114 and X(max) 118, or at 60 decibals.

FIG. 12 illustrates another exemplary channel, this channel being the channel whose center frequency is set at 178 Hertz. The graph of FIG. 12 corresponds in representation to that illustrated from the graph in FIG. 11. Again, curve 311 represents the amplitudes when this individual channel is the highest ranking channel, curve 312 represents the amplitudes when this channel is the second ranking, curve 313 when it is the third ranking and so on through curve 320. With the behavior exhibited by the channel of FIG. 12, it can be seen that the distributions are not contingent, i.e., there is little contingent relationship between amplitude and rank. There is no decibel level at which a threshold will be set in which most of the instances in which the channel is highest ranked could be achieved and those at when which it is lower rank could be achieved A noncontingent channel as the channel illustrated in FIG. 12 may be either entirely excluded from the sum, included entirely in the sum or, perhaps, included but at a reduced level, thus, reducing the possibility of confusion due to its contained periodicities.

Figure 10:
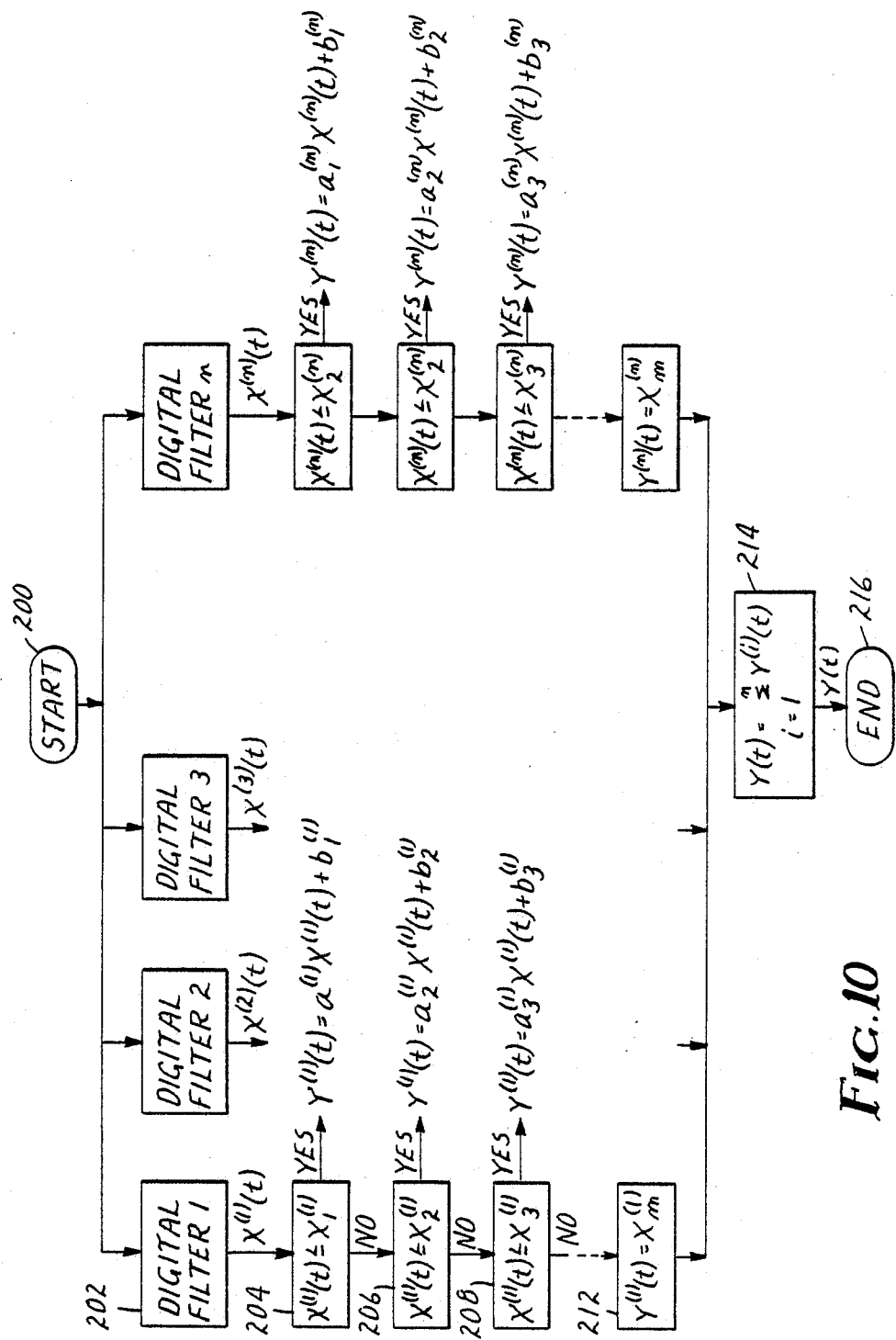
FIG. 10 is a flow chart illustrating how the nonlinearity of FIG. 9 is defined.

With the X values 114, 116 and 118 and the Y values 108, 110 and 112 determined as specified above, a flow chart for a program to digitally implement the function of the nonlinearities 90 is illustrated in FIG. 10. Digital program operates by starting at block 200 and individually implementing sequentially each individual channel A-I. Since each individual channel is identical to the other, only one channel implementation, namely channel A will be described. A digital filter is implemented by block 202 which corresponds to filter 88A. This digital implementation is conventional and well known in the art. For the first channel, the program in block 204 takes the output from block 202 and implements the linear function 100 of FIG. 9 by determining if the X value is within the range of the linear function 100. If yes, the program determines the output function Y(t) by obtaining constant values A1 and B1 and applying them to the formula A1 x X(t)+B1. If the value of X(t) is not within the range of the linear function 100, then block 206 determines if the X values are within the range of the first power function 102. If yes, then the program determines the Y output value by looking up values A2 and B2 in a table and applying it to the formula Y(t)=A2 x X(t)+B2. Preferably this can be accomplished by a plurality of piecewise linear segments to approximate a logrithmic curve. Similarly, the second power function 104 is implemented in block 208, if appropriate by using the table look up for the values A3 and B3. Also preferably a logrithmic curve may be approximated with linear segments Finally, the program implement the saturation function 106 by block 212 if the X value X(t) is within the value of the saturation portion by simply outputting a known constant since the curve is saturated. The program then repeats each of these individual blocks for each individual channel contained within the digital signal processor 10.

In the preferred embodiment, the program illustrated in FIG. 10 is implemented on an integrated circuit which forms and operates as signal processor 10. This integrated circuit is a model 320C10 integrated circuit manufactured by Texas Instrument Corporation, Dallas, Tex. In the program of FIG. 10, the value obtained from each individual channel is then digitally summed at block 214 to obtain the final Y(t) and the program is ended at block 216 and, hence, repeats.

Figure 13:
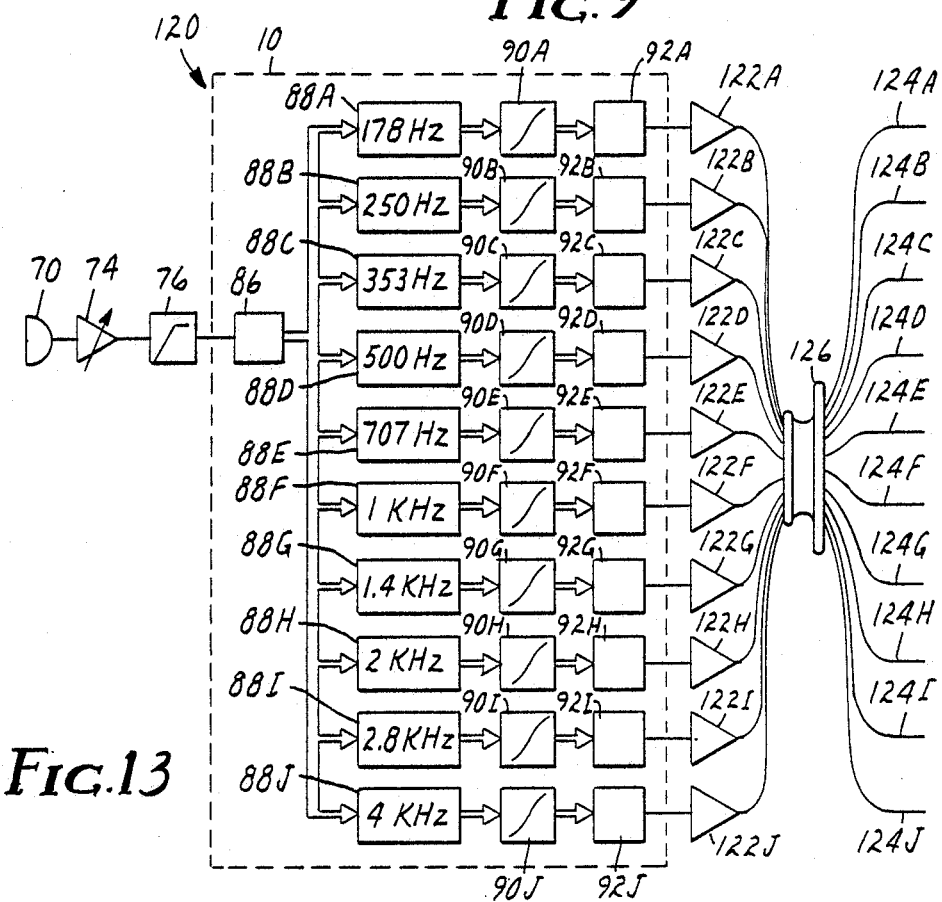
FIG. 13 is a block diagram of an alternative embodiment of the present invention.

An alternative embodiment of the auditory prosthesis 120 is illustrated in FIG. 13. The auditory prosthesis 120 is similar to the auditory prosthesis 68 of FIG. 8 in that it has a microphone 70 and automatic gain control circuit 74, a pre-emphasis of filter 76 and a signal processor 10. Signal processor 10 contains a single analog to digital converter 86 which supplies the electrical input signal to 10 filters 88A-88J. The center frequencies at 178 Hertz, 250 Hertz, 353 Hertz, 500 Hertz, 707 Hertz, 1 kiloHertz, 1.4 kiloHertz, 2 kloHertz, 2.8 kiloHertz and 4 kiloHertz, respectively. Each filter 88 is supplied to a nonlinearity 90A-90J individually. Filters 88 and nonlinearities 90 operate identical to the filters 88 and nonlinearities 90 illustrated in FIG. 8. However, in the embodiment illustrated in FIG. 11 the output of the individual nonlinearities instead of being summed together are individually passed to digital to analog converters 92A-92J. Alternatively one digital to analog converter 92 could be time division multiplexed and, hence, coupled to all nonlinearities 90A-90J. The output of each individual digital to analog converter 92A-92J is supplied to an individual current source 122A-122J which individually supply an electrode 124A-124J. Thus, each individual filter 88A-88J ultimately supply an individual electrode 124A-124J. Thus, an individual electrode, e.g., 124A, would contain only the periodicities of one filter, namely, resonator 88A. The wires supplying electrodes 124A-124J are illustrated passing through a percutaneous plug 126. Electrodes 124A-124J while illustrated in FIG. 11 as a single wire will exist in the patient as an electrode pair since they must pass current from one individual electrode element to a second individual electrode element. Thus, electrode 124A may represent a wire element pair designed to be positioned within the cochlea. Alternatively, electrodes 124A-124J may represent single electrode elements which pass current from their individual elements to a single common return electrode (not shown).

While the description of the preferred embodiment is described as electrically stimulating a person as in a cochlear implant, it is to be recognized and understood that the present invention is also applicable to acoustic stimulation as in a hearing aid.

While the description of the preferred embodiment is described as having the predetermined characteristics of the nonlinearities and/or filters as being set for all time, it is to be recognized and understood that these predetermined values could advantageously be recomputed occasionally, periodically or upon the occurrence of a certain event and still be predetermined in the intervals in between.

Throughout this description, it has been preferred that filters 88 be sharply tuned, high Q filters which function as resonators. It is to be recognized and understood, however, that the present invention will also operate advantageously with bandpass filters which are not as sharply tuned, which do no have high Q's or which do not function as resonators. The channel dominance selection of nonlinearities 90 still operate to simplify the resulting signal to be supplied to the auditory central nervous system Thus, there has been shown and described a novel signal processor for an auditory prosthesis utilizing channel dominance. It is to be recognized and understood, however, that various changes, modifications and substitutions in the form and in the details of the present invention may be made by those skilled in the art without departing from the scope of the following claims.

What is claimed is:

1. An auditory prosthesis adapted to receive a sound signal and transform and transmit said sound signal to a signal representing sound to a person, comprising:
   transducer means adapted to receive said sound signal for transforming said sound signal to an electrical signal;
   a plurality of filters, each passing a different center frequency, each operatively coupled to receive said electrical signal and each providing a filtered signal representative of the auditory content of said electrical signal relative to its respective center frequency;

a plurality of gating means, being individually coupled to said filtered signals of said plurality of filters, for passing an output signal at a level above the perceptual level of said person only when said filtered signal is above a predetermined level, said predetermined level being individually determined such that said output is passed above said perceptual level only when the level of said filtered signal to which said gating means is coupled is likely to be among the largest of said filtered signals of all of said plurality filters, each of said output signals being adapted to be utilized in said auditory prosthesis;

coupling means operatively coupled to said plurality of gating means for receiving all of said output signals and transmitting said output signals in a form which may be adapted to be supplied to said person.

2. An auditory prosthesis as in claim 1 wherein said coupling means, comprises:

summing means operatively coupled to said plurality of gating means for summing all of said threshold output signals and providing a single output signal; and electrode means operatively coupled to said summing means for supplying said single output signal in a form which may be adapted to be supplied to said person.

3. An auditory prosthesis as in claim 1 wherein said coupling means, comprises:

a plurality of current sources selectively coupled to said output signals of said plurality of gating means for supplying a plurality of stimulating signals; and a plurality of electrode pairs selectively coupled to said plurality of stimulating signals and adapted to be electrically provided to an auditory nerve of said person.

4. An auditory prosthesis as in claim 2 wherein said plurality of gating means individually utilize said predetermined threshold by means of a table look-up mechanism.

5. An auditory prosthesis as in claim 2 in which each of said gating means further comprises a nonlinearity, for introducing a nonlinearity into said filtered signal which is above said perceptual level.

6. An auditory prosthesis as in claim 5 wherein said nonlinearity has a linear function portion, a compressive nonlinear function portion and a saturation function portion.

7. An auditory prosthesis as in claim 5 which further comprises an analog to digital convertor means coupled between said electrical input signal and said plurality of filters for converting said electrical input signal from analog to digital form, wherein said plurality of filters and said plurality of gating means operate on said digital form of said electrical input signal and which further comprises a digital to analog converter means coupled to said output signals of said gating means.

8. An auditory prosthesis for receiving an auditory signal representing sound and supplying an electrical signal which is adapted to stimulate the auditory nerve of a person, comprising:

transducer means adapted to receive said auditory signal for transforming said auditory signal to an electrical input signal;

generation means operatively coupled to said electrical input signal for generating a plurality of electrical signals selectively replicating the normal temporal nerve discharge pattern of auditory nerve fibers of individual locations within a normally functioning cochlea of a person;

a plurality of gating means, being individually coupled to said filtered signal of said plurality of filters, for passing an output signal at a level above the perceptual level of said person when said filtered signal is above a predetermined level, said predetermined level being individually determined such that said output is passed above said perceptual level only when the level of said filtered signal to which said gating means is coupled is likely to be among the largest of said filtered signals of all of said plurality filters, each of said output signals being adapted to be utilized in said auditory prosthesis;

stimulation means, operatively coupled to said output signal, for stimulating selected auditory nerve sites within the cochlea corresponding to said individual locations.

9. An auditory prosthesis as in claim 8 wherein said stimulation means comprises:

summing means, operatively coupled to said output signal for combining said output signal into a composite electrical signal; and an electrode pair coupled to said composite electrical signal suitable for supplying an electrical stimulation current and adapted to stimulate the auditory nerve.

10. An auditory prosthesis as in claim 9 wherein said summing means combines said output signal into said composite electrical signal by adding the amplitude of said plurality of electrical signals.

11. An auditory prosthesis as in claim 8 wherein said stimulation means comprises a plurality of electrode pairs selectively coupled to said plurality of electrical signals, each of said plurality of electrode pairs being capable of supplying a suitable stimulation current to a selected auditory nerve site.

12. An auditory prosthesis as in claim 8 wherein said generation means produces said plurality of electrical signals, each having periodic oscillations at a particular frequency band corresponding in amplitude to the corresponding energy at the respective said particular frequency band of said electrical input signal, the period of periodic oscillation corresponding to the period of the temporal nerve discharge pattern at said individual locations.

* * * * *

UNITED STATES PATENT AND TRADEMARK OFFICE
CERTIFICATE OF CORRECTION

PATENT NO. : 4,813,417
DATED : March 21, 1989
INVENTOR(S) : Sigfrid D. Soli and Christopher van den Honert It is certified that error appears in the above-identified patent and that said Letters Patent is hereby corrected as shown below:

Col. 9, line 65, "kloHertz" should read --kiloHertz--.

Col. 10, line 45 "no" should read --not--.

Signed and Sealed this

Twenty-first Day of November, 1989

Attest:

JEFFREY M. SAMUELS

Attesting Officer       Acting Commissioner of Patents and Trademarks

UNITED STATES PATENT AND TRADEMARK OFFICE
CERTIFICATE OF CORRECTION

PATENT NO. : 4,813,417

DATED : March 21, 1989

INVENTOR(S) : Sigfrid D. Soli and Christopher van den Honert

It is certified that error appears in the above-identified patent and that said Letters Patent is hereby corrected as shown below:

Column 6, line 43, change "In" to read -- An --.

Column 12, between lines 9 and 10, insert -- a plurality of filters, each passing a different center frequency, each operatively coupled to receive said electrical signal and each providing a filtered signal representative of the auditory content of said electrical signal relative to its respective center frequency; --.

Column 12, line 17, change "signal" to read -- signals --.

Signed and Sealed this

Twenty-first Day of September, 1993

*Attest:*

BRUCE LEHMAN

*Attesting Officer*     *Commissioner of Patents and Trademarks*